United States Patent
Orenga et al.

(10) Patent No.: US 7,691,601 B2
(45) Date of Patent: Apr. 6, 2010

(54) MEDIUM FOR DETECTING AND/OR IDENTIFYING OF MICROORGANISMS

(75) Inventors: Sylvain Orenga, Neuville-sur-Ain (FR); Celine Roger-Dalbert, Vaux-en-Bugey (FR); John Perry, Newcastle-Upon-Tyne (GB); Arthur James, Cockermouth (GB)

(73) Assignee: Biomerieux, Marcy l'Etoile (FR)

( * ) Notice: Subject to any disclaimer, the term of this patent is extended or adjusted under 35 U.S.C. 154(b) by 517 days.

(21) Appl. No.: 10/552,508

(22) PCT Filed: Apr. 2, 2004

(86) PCT No.: PCT/FR2004/050139

§ 371 (c)(1),
(2), (4) Date: Oct. 5, 2005

(87) PCT Pub. No.: WO2004/092400

PCT Pub. Date: Oct. 28, 2004

(65) Prior Publication Data
US 2006/0257966 A1    Nov. 16, 2006

(30) Foreign Application Priority Data
Apr. 7, 2003 (FR) .................................. 03 04263

(51) Int. Cl.
*C12Q 1/04* (2006.01)
*C12Q 1/10* (2006.01)

(52) U.S. Cl. .................. 435/34; 435/253.6; 435/29

(58) Field of Classification Search .................. None
See application file for complete search history.

(56) References Cited

U.S. PATENT DOCUMENTS

| 5,854,011 A * | 12/1998 | Chen et al. ..................... 435/24 |
| 2001/0041353 A1 * | 11/2001 | McCarthy .................. 435/69.1 |
| 2002/0076796 A1 * | 6/2002 | Kapeller-Libermann et al. .......... 435/226 |

FOREIGN PATENT DOCUMENTS

WO    WO 02/240706 A   *   5/2002

OTHER PUBLICATIONS

Cooke et al. (1999) Appl. Env. Microbiol. 65(2): 807-812.*
Kardos et al. (2000) Toxicological Sciences 58(1): 118-126.*
Yves Le Merrer et al.; "Synthesis of Azasugars as Potent Inhibitors of Glycosidases"; *Bioorganic & Medicinal Chemistry*; vol. 5, No. 3; pp. 519-533; 1997.
Kare Sondergaard et al.; "Synthesis of 5-Azacastanospermine, a Conformationally Restricted Azafagomine Analogue"; *Chem. Eur. J.*; vol. 7, No. 11; pp. 2324-2331; 2001.

* cited by examiner

*Primary Examiner*—Lisa J Hobbs
(74) *Attorney, Agent, or Firm*—Oliff & Berridge, PLC

(57) ABSTRACT

The invention relates to a medium for detecting and/or identifying microorganisms present in a sample, comprising a culture medium and at least one substrate that can be hydrolysed to a labelled product by at least a first enzyme not free in the sample, and specific for the microorganisms, characterized in that it also comprises at least one inhibitor of at least a second enzyme, different from the first enzyme or identical to it, but free in said sample and not originating from a microorganism. The present invention also finds a preferred application in the field of biomedical diagnosis or in food microbiology, and more particularly in bacteriology and mycology.

15 Claims, No Drawings

MEDIUM FOR DETECTING AND/OR IDENTIFYING OF MICROORGANISMS

The field of the invention is that of microbiological analysis by biochemical process, and in particular of the detection and identification of microorganisms by seeding of reaction mediums.

In the context of the invention, interest is more particularly focused on detecting and identifying microorganisms, such as in particular bacteria or yeast, that are pathogens or indicators of quality, whether in the medical environment or the industrial environment.

A large number of media for detecting these microorganisms currently exist. This detection can be based in particular on the use of particular substrates specific for an enzyme of the microorganism that it is desired to detect. In general, synthetic substrates for enzymes consist of a first part specific for the enzymatic activity to be revealed, and of a second part that acts as a label, and is generally chromogenic or fluorescent. By virtue of the choice of these substrates, according to whether or not there is reaction, it is possible to characterize the nature of a microorganism.

Thus, in the case of bacteria, *Escherichia coli* strains are often demonstrated by revealing an enzymatic activity of the osidase type, such as β-glucuronidase activity or β-galactosidase activity. Similarly, the *Listeria* genus can be detected by demonstrating β-glucosidase activity.

Aminopeptidase activity can also be used to reveal a group, a genus or a species of bacteria. Thus, alanine-aminopeptidase activity, for example, makes it possible to differentiate Gram-negative bacteria from Gram-positive bacteria.

Finally, mention may also be made of the detection of esterase activity for in particular demonstrating the *Salmonella* genus. This is because the *Salmonella* genus possesses non-specific esterases capable of hydrolysing chromogenic synthetic substrates, for example indigogenic substrates. In the case of the detection of salmonellae, and more particularly in the case of bacteria with esterase activity, the detection and/or the identification of these bacteria is conventionally carried out on isolating agar or liquid media, which make it possible to detect and/or identify colonies suspected of being bacteria with esterase activity.

However, when certain samples are taken, in particular stool samples, the presence of enzymes not specific for the microorganism that it is desired to detect, and free in the sample (reference is then made to "free enzymes") and that can subsequently react with the chromogenic substrate, are observed. These "free" enzymes can in particular be present in a biological sample, such as a stool sample, and can come from cells of the digestive tract, of the liver and of the pancreas, and can therefore find themselves in the biological sample, via these organs. Free enzymes can also be present in food samples that it is desired to analyse, such as, for example, poultry livers; in this case, the enzymes are derived from the cells of the liver. This induces the suspicion of positives that cannot be confirmed: some samples are considered to be contaminated, when in fact they are not, which can have dramatic consequences for the subsequent diagnosis. Thus, in the case of the detection of salmonellae demonstrated by esterase-type enzymatic activity, the stool sample not contaminated with salmonellae may contain "free" esterases that then hydrolyse the substrate present in the culture medium, which causes the release of a magenta colour, normally specific for salmonellae.

The present invention therefore proposes to improve the media for detecting microorganisms currently sold, by limiting the presence of false positives engendered by the presence of free enzymes in the sample and not specific for a microorganism. Surprisingly, the inventors have demonstrated that the use of certain chemical compounds inhibits the free enzymes of the sample, without inhibiting the non-free enzymes, i.e. the enzymes originating from the microorganisms that it is desired to detect.

To this effect, the present invention relates to a medium for detecting microorganisms present in a sample, such as in particular a biological or food sample, comprising a culture medium and at least one substrate that can be hydrolysed to a labelled product by at least a first enzyme not free in the sample, and specific for said microorganisms, characterized in that it also comprises at least one inhibitor of at least a second enzyme, free in said sample and not originating from the desired microorganism. This second enzyme may be different from said first enzyme or identical to it.

For the purpose of the present invention, the term "microorganism" covers bacteria, yeast and, more generally, organisms that are generally single-cell organisms invisible to the naked eye, which can be multiplied and manipulated in the laboratory.

According to a preferred embodiment of the invention, the microorganism is a Gram-negative or -positive bacterium, or a yeast.

By way of Gram-negative bacteria, mention may be made of bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Branhamella, Neisseria, Burkholderia, Citrobacter, Hafnia, Edwardsiella* and *Legionella*.

By way of Gram-positive bacteria, mention may be made of bacteria of the following genera: *Enterococcus, Streptococcus, Staphylococcus, Bacillus, Listeria, Clostridium, Mycobacteria* and *Corynebacteria*.

By way of yeast, mention may be made of yeast of the following genera: *Candida, Cryptococcus, Saccharomyces* and *Trichosporon*.

According to a preferred embodiment of the invention, the microorganism is a bacterium, which preferably belongs to the *Salmonella* genus, or a yeast, which preferably belongs to the *Candida* genus.

For the purposes of the present invention, the term "culture medium" is intended to mean a medium comprising all the elements required for the survival and/or for the growth of microorganisms. In practice, those skilled in the art would choose the culture medium as a function of the target microorganisms, according to criteria that are entirely known and within the scope of those skilled in the art. For bacteria, mention may be made, by way of indication, of selective media of the type: MacConkey, Columbia ANC, PALCAM, and non-selective media of the trypcase soy type, a nutritive medium. For yeast, mention may be made, as culture medium, of Sabouraud gentamycin-chloramphenicol, or Sabouraud.

The culture medium according to the invention may contain optional other additives such as, for example: peptones, one or more growth factors, carbohydrates, one or more selective agents, buffers, one or more gelling agents, etc. This culture medium may be in the form of a ready-to-use gel liquid, i.e. ready for seeding in a tube or flask, or on a Petri dish.

For the purpose of the present invention, the "substrate" is chosen from any substrate that can be hydrolysed to a product that makes it possible to directly or indirectly detect a microorganism. Preferably, this substrate comprises:
- a first portion specific for the enzymatic activity to be revealed. This first portion is capable of interacting with said first enzyme, which is specific for the microorganism sought, but also with said second enzyme,
- a second portion that acts as a label, hereinafter referred to as label portion, which may be fluorescent or chromogenic.

As fluorescent substrate, mention may in particular be made of substrates based on umbelliferone or on aminocoumarin, based on resorufin or else based on fluorescein. As chromogenic substrate, that is more suitable for solid supports (filter, agar, electrophoresis gel), mention may in particular be made of substrates based on indoxyl and its derivatives, and substrates based on hydroxyquinoline or on esculetin and their derivatives, which make it possible to detect osidase and esterase activities. Mention may also be made of substrates based on nitrophenol and nitroaniline and derivatives, for detecting osidase and esterase activities in the case of nitrophenol-based substrates, and peptidase activities in the case of nitroaniline-based substrates. Finally, mention may be made of substrates based on naphthol and naphthylamine and its derivatives, which make it possible to detect osidase and esterase activities via naphthol, and peptidase activities via naphthylamine. This substrate may in particular, but without implied limitation, make it possible to detect enzymatic activity such as the activity of an osidase, peptidase, esterase, etc.

The term "sample" is intended to mean any type of sample in which it is desired to detect the presence of microorganisms. This sample may be a biological or food sample. This sample may originate in particular, but without implied limitation, from a blood sample, urine sample, stool sample, food sample, etc.

The term "first enzyme" is intended to mean an enzyme that is not free in the sample, i.e. that originates from the microorganism that it is desired to detect. This enzyme may in particular, but without implied limitation, be an osidase, peptidase, esterase, sulphatase, phosphatase, etc. This enzyme makes it possible to hydrolyse the substrate to a labelled product.

The term "second enzyme" is intended to mean an enzyme that is different from the first enzyme or identical to it, but free in the sample, i.e. it does not originate from the microorganism sought. This second enzyme is capable of reacting with the substrate, which can induce the presence of false positives. This enzyme may in particular, but without implied limitation, be an osidase, peptidase, esterase, sulphatase, phosphatase, etc.

According to a preferred embodiment of the invention, said first enzyme is an esterase. Preferably, the inhibitor then belongs to the organophosphate family, and is a compound of formula (I)

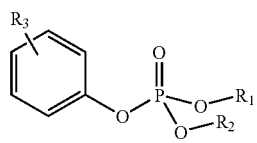

(I)

in which $R_1$ is a hydrogen atom, or an alkyl, aryl or halogen group, $R_2$ is a hydrogen atom, or an alkyl, aryl or halogen group, $R_3$ is nothing, or an alkyl, aryl or $NO_2$ group.

According to the invention, the term "aryl" is intended to mean in particular an aromatic $C_6$-$C_{10}$ ring, in particular phenyl, benzyl, 1-naphthyl or 2-naphthyl.

The term "alkyl" is intended to mean a $C_1$-$C_6$ alkyl, i.e. a straight or branched alkyl having from 1 to 6 carbon atoms. By way of example, mention may be made of methyl, ethyl, propyl, isopropyl, butyl, t-butyl, pentyl, isopentyl and hexyl.

According to a preferred embodiment of the invention, the inhibitor is a compound of formula (I) in which
- $R_1$ and $R_2$ are ethyl groups,
- $R_3$ is an $NO_2$ group.

This compound is O,O-diethyl p-nitrophenyl phosphate having the formula below:

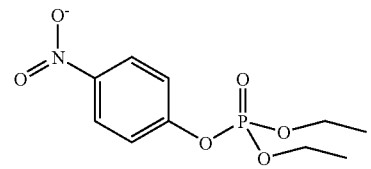

According to a preferred embodiment of the invention, the inhibitor is a compound of formula (I) in which
- $R_1$ and $R_2$ are methyl groups,
- $R_3$ is an $NO_2$ group.

This compound is O,O-dimethyl p-nitrophenyl phosphate having the formula below:

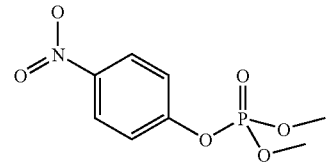

According to another preferred embodiment of the invention, the inhibitor is a compound of formula (I) in which
- $R_1$ and $R_2$ are chloroethyl groups,
- $R_3$ is a ring of formula

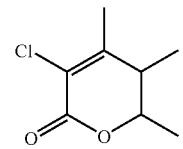

The dotted lines make it possible to visualize the position of said ring in the compound of formula (I) of the invention.

This compound is O,O-di-(2-chloroethyl)-O-(3-chloro-4-methylcoumarin-7-yl) phosphate having the formula below:

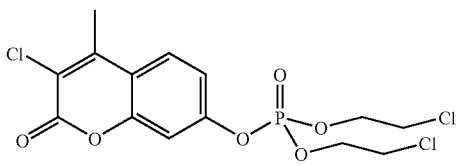

The inhibitor may also be a derivative of the molecules presented above.

The concentration of O,O-diethyl p-nitrophenyl phosphate or its derivative in the detection medium is preferably between 0.1 and 15 mg/l, and even more preferably between 1 and 10 mg/l.

The concentration of O,O-dimethyl p-nitrophenyl phosphate or its derivative in the detection medium is preferably between 0.1 and 100 mg/l, and even more preferably between 10 and 50 mg/l.

The concentration of O,O-di-(2-chloroethyl)-O-(3-chloro-4-methylcoumarin-7-yl) phosphate or its derivative in the detection medium is preferably between 1 and 1000 mg/l, even more preferably between 30 and 100 mg/l.

According to a preferred embodiment of the invention, said first enzyme is an osidase, preferably a glucosidase, and even more preferably a-glucosidase. Those skilled in the art may refer to the publication by Le Merrer et al, 1997, Bioorganic & Medical Chemistry, Vol. 5, (3), pp 519-533 in choosing a glucosidase inhibitor.

Preferably, the inhibitor is a castanospermine, i.e. a compound of formula (II):

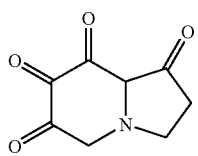
(II)

or a derivative of this compound.

Castanospermine derivatives are in particular described in the publication by Sondergaard et al., Chem Eur J 2001, 7 No. 11.

The concentration of castanospermine or its derivative in the detection medium is preferably between 0.5 and 30 g/l, and even more preferably between 1 and 10 g/l.

According to a preferred embodiment of the invention, said substrate is a chromogenic substrate, preferably an ester of indoxyl or of its derivatives, and even more preferably an indoxyl ester having formula (III) below

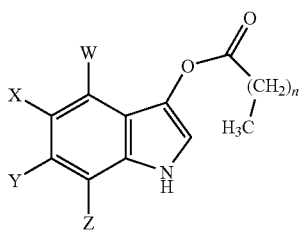
(III)

in which n is between 1 and 12, and W, X, Y and Z are chosen from H, Br, Cl, F and I. Even more preferably, the substrate is 5-bromo-6-chloro-3-indoxyl caprylate ((Magenta C8, CAS No. 209347-94-4) or 5-bromo-3-indoxyl nonanoate (Biosynth).

The invention also relates to a method for detecting and/or identifying microorganisms, comprising:
- seeding said microorganisms to be identified on a detection medium, as defined above,
- incubating the detection medium seeded with said microorganisms to be identified, and
- determining the presence of said microorganisms by detecting the substrate(s) hydrolysed to a labelled product.

The seeding of the microorganisms, such as in particular the bacteria or yeast, can be carried out by any of the seeding techniques well known to those skilled in the art. Similarly, the incubation is preferably carried out at a temperature for which the growth of the microorganisms and the enzymatic activity that it is desired to detect are at a maximum, which those skilled in the art can readily choose according to the enzymatic activity to be detected. By way of indication, the incubation is preferably carried out at between 36 and 38° C.

The invention relates to the use of the detection and/or identification medium as defined above, for identifying microorganisms.

The invention also relates to the use of a compound of formula (I)

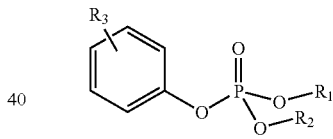

in which $R_1$ is a hydrogen atom, or an alkyl, aryl or halogen group, $R_2$ is a hydrogen atom, or an alkyl, aryl or halogen group, $R_3$ is nothing, or an alkyl, aryl or $NO_2$ group, for inhibiting a free enzyme, preferably a free esterase in a sample as defined above.

The invention also relates to the use of a compound of formula (II)

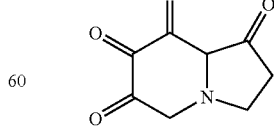
(II)

for inhibiting a free enzyme, preferably a free osidase, preferably a free glucosidase, and even more preferably a free α-glucosidase in a sample as defined above.

The examples below are given by way of explanation and are in no way limiting in nature. They will make it possible to understand the invention more clearly.

EXAMPLE 1

Inhibition of Free Esterases in a Sample, with O,O-diethyl p-nitrophenyl phosphate, during the Identification of *Salmonella* Bacteria The aim of the experiment presented in this example is to determine the inhibitory effect of O,O-diethyl p-nitrophenyl phosphate (Paraoxon® ethyl; Riedel-de Haën, St Quentin Fallavier, France) on free esterases (in a stool sample contaminated with salmonellae).

Preparation of the detection medium: A volume of 250 ml of detection medium is prepared from a powdered medium having the following composition:

| | |
|---|---|
| Peptones | 6.25 g/l |
| Tris | 0.16 g/l |
| Lactose | 6 g/l |
| Bile salts | 1.5 g/l |
| NaCl | 5 g/l |
| Agar | 14 g/l |

Melting is carried out at 100° C., and the medium is autoclaved at 121° C. for 15 minutes. The additives are then added to the medium: Magenta C8 (500 mg/l; B-7102, BIOSYNTH, Staad, Switzerland); X-glucoside (75 mg/l; B-7250, BIOSYNTH, Staad, Switzerland); cefsulodine (10 mg/l; C 4786, Sigma, St Quentin Fallavier, France) and various concentrations of the inhibitor O,O-diethyl p-nitrophenyl phosphate (Paraoxon® ethyl; CAS No. 311-45-5; 36186, Riedel-de Haën, St Quentin Fallavier, France; 0; 1; 5 or 10 mg/l).

The various detection media thus obtained are then poured into Petri dishes.

Seeding of *Salmonella* bacteria: 10 μl of stools are deposited onto a Petri dish, this stool suspension is mixed or not mixed with 10 μl of a suspension of *Salmonella* (0.5 McF) and isolated as 3 dials on a Petri dish. Various salts and various *Salmonella* strains originating from the applicant's collection are used according to this protocol. The Petri dishes are incubated at 37° C. for 24 hours. The appearance of a coloration at the point of deposit of the stool ("deposit" column) and at the *Salmonella* colony ("colony" column) is read according to a semi-quantitative scale:

0=no coloration
0.5=trace of coloration
1=weak coloration
2=strong coloration

The results obtained are given in Table 1.

TABLE 1

Effects of the inhibitor O,O-diethyl p-nitrophenyl phosphate on the activity of the free esterases in a stool sample during the identification of *Salmonella* bacteria

| | | [O,O-Diethyl p-nitrophenyl phosphate] in mg/l | | | | | | | |
|---|---|---|---|---|---|---|---|---|---|
| | | 0 | | 1 | | 5 | | 10 | |
| Strain | Stool No. | Deposit | Colonies | Deposit | Colonies | Deposit | Colonies | Deposit | Colonies |
| Absence | A | 1 | 0 | 0.5 | 0 | 0 | 0 | 0 | 0 |
| | B | 0 | 0 | 0 | 0 | 0 | 0 | 0 | 0 |
| *Salmonella Enteritidis* | A | 1 | 2 | 0.5 | 2 | 0 | 2 | 0 | 2 |
| | B | 0 | 2 | 0 | 2 | 0 | 2 | 0 | 2 |
| *Salmonella Paratyphi* A | A | 1 | 2 | 0.5 | 1 | 0 | 1 | 0 | 1 |
| | B | 0 | 2 | 0 | 1 | 0 | 1 | 0 | 1 |
| *Salmonella Typhi* | A | 1 | 1 | 0.5 | 1 | 0 | 1 | 0 | 1 |
| | B | 0 | 1 | 0 | 1 | 0 | 1 | 0 | 1 |

As shown in Table 1, the coloration is decreased at the point of deposit of the stool in the presence of the inhibitor, whereas it is maintained in the bacterial colonies whether the inhibitor is present or absent. The enzymes that are free in the stools (referred to in the disclosure of the invention as "second enzyme, free"), and that are mainly at the point of deposit of the stool are therefore clearly inhibited by the inhibitor, whereas the enzymes originating from the bacteria (referred to in the disclosure of the invention as "first enzyme not free"), and that are mainly in the salmonella colonies, are not inhibited.

The coloration at the site of the deposit, observed when the stools are deposited in the absence of strain, demonstrates the presence of a reaction related to the presence of free enzymes from the sample, which do not originate from the contamination with salmonellae.

These results demonstrate that the aspecific enzymatic reactions due to the presence of "free enzymes" are greatly inhibited in the presence of the inhibitor O,O-diethyl p-nitrophenyl phosphate, which limits the detection of false positives.

EXAMPLE 2

Inhibition of Free Esterases in a Sample, with O,O-dimethyl p-nitrophenyl phosphate during the Identification of *Salmonella* Bacteria The aim of the experiments presented in this example is to demonstrate the free esterase-inhibiting effect of O,O-dimethyl p-nitrophenyl phosphate (Paraoxon® methyl; Riedel-de Haën, St Quentin Fallavier, France) on stools contaminated with salmonellae.

Preparation of the detection medium: A volume of 250 ml of detection medium is prepared from a powdered medium having the following composition:

| | |
|---|---|
| Peptones | 6.25 g/l |
| Tris | 0.16 g/l |
| Lactose | 6 g/l |
| Bile salts | 1.5 g/l |

-continued

| | |
|---|---|
| NaCl | 5 g/l |
| Agar | 14 g/l |

Melting is carried out at 100° C., and the medium is autoclaved at 121° C. for 15 minutes. The additives are then added to the medium: Magenta C8 (500 mg/l; B-7102, BIOSYNTH, Staad, Switzerland); X-glucoside (75 mg/l; B-7250, BIOSYNTH, Staad, Switzerland); cefsulodine (10 mg/l; C 4786, Sigma, St Quentin Fallavier, France) and various concentrations of the inhibitor O,O-dimethyl p-nitrophenyl phosphate (Paraoxon® methyl; CAS No. 950-35-6; Riedel-de Haën, St Quentin Fallavier, France; 5, 10, 25 mg/l).

The various detection media thus obtained are then poured into Petri dishes.

Seeding of *Salmonella* bacteria: The Petri dishes are inoculated, incubated and read as in Example 1.

The results obtained are given in Table 2.

TABLE 2

Effects of the inhibitor O,O-dimethyl p-nitrophenyl phosphate on the activity of the free esterases in a sample during the identification of *Salmonella* bacteria

| | | [O,O-Dimethyl p-nitrophenyl phosphate] in mg/l | | | | | | | |
|---|---|---|---|---|---|---|---|---|---|
| Strain | Stool | 0 | | 5 | | 10 | | 25 | |
| No. | No. | Deposit | Colonies | Deposit | Colonies | Deposit | Colonies | Deposit | Colonies |
| None | C | 2 | 0 | 1 | 0 | 0.5 | 0 | 0 | 0 |
| | D | 2 | 0 | 1 | 0 | 1 | 0 | 0 | 0 |
| *Salmonella Typhi* | C | 2 | 0.5 | 1 | 0.5 | 0.5 | 1 | 0 | 0.5 |
| | D | 2 | 0.5 | 1 | 0.5 | 1 | 0.5 | 0 | 0.5 |
| *Salmonella Enteritidis* | C | 2 | 2 | 1 | 2 | 0.5 | 2 | 0 | 2 |
| | D | 2 | 2 | 1 | 2 | 1 | 2 | 0 | 2 |

As shown in Table 2, the coloration is decreased at the point of deposit of the stool in the presence of the inhibitor, whereas it is maintained in the bacterial colonies, whether the inhibitor is present or absent. The free enzymes in the stools are therefore clearly inhibited by the inhibitor, whereas the enzymes originating from the bacteria are not inhibited.

These results show that the aspecific enzymatic reactions due to the presence of "free enzymes" are greatly inhibited in the presence of the inhibitor O,O-dimethyl p-nitrophenyl phosphate, which limits the detection of false positives.

EXAMPLE 3

Inhibition of Free Esterases in a Sample, with O,O-di-(2-chloroethyl)-O-(3-chloro-4-methylcoumarin-7-yl)phosphate During the Identification of *Salmonella* Bacteria The aim of the experiments presented in this example is to demonstrate the inhibitory effect of O,O-di-(2-chloroethyl)-O-(3-chloro-4-methylcoumarin-7-yl)phosphate (Haloxon®; Sigma, St Quentin Fallavier, France) on free esterases in a sample (stools) contaminated with salmonellae.

Preparation of the detection medium: 250 ml of the medium of Example 1, in which the O,O-diethyl p-nitrophenyl phosphate is replaced with various concentrations of O,O-di-(2-chloroethyl)-O-(3-chloro-4-methylcoumarin-7-yl) phosphate (Haloxon®; CAS No. 321-55-1; R276995, Sigma, St Quentin Fallavier, France; 0; 1; 10; 100 or 1000 mg/l), are prepared according to the method of Example 1.

The various selection media thus obtained are then poured into Petri dishes.

Seeding of Salmonella bacteria: The Petri dishes are inoculated, incubated and read as in Example 1.

The results obtained are given in Table 3.

TABLE 3

Effects of the inhibitor O,O-di-(2-chloroethyl)-O-(3-chloro-4-methylcoumarin-7-yl) phosphate on the activity of the free esterases in a sample during the identification of *Salmonella* bacteria

| | | [O,O-Di-(2-chloroethyl)-O-(3-chloro-4-methylcoumarin-7-yl) phosphate] in mg/l | | | | | | | | |
|---|---|---|---|---|---|---|---|---|---|---|
| | Stool | 0 | | 1 | | 10 | | 100 | | 1000 | |
| Strain No. | No. | Deposit | Colonies | Deposit | Colonies | Deposit | Colonies | Deposit | Colonies | Deposit | Colonies |
| Absence | A | 2 | 0 | 1 | 0 | 1 | 0 | 0.5 | 0 | 0 | 0 |
| | B | 2 | 0 | 1 | 0 | 0.5 | 0 | 0 | 0 | 0 | 0 |
| Salmonella Enteritidis | A | 2 | 2 | 1 | 2 | 1 | 2 | 0.5 | 2 | 0 | 2 |
| | B | 0 | 2 | 0 | 2 | 0 | 2 | 0 | 2 | 0 | 2 |
| Salmonella Paratyphi A | A | 2 | 2 | 1 | 2 | 1 | 2 | 0.5 | 1 | 0 | 0.5 |
| | B | 0 | 2 | 0 | 2 | 0 | 2 | 0 | 1 | 0 | 0.5 |
| Salmonella Typhi | A | 2 | 1 | 1 | 1 | 1 | 1 | 0.5 | 1 | 0 | 1 |
| | B | 0 | 1 | 0 | 1 | 0 | 1 | 0 | 1 | 0 | 1 |

As shown in Table 3, the coloration is decreased at the point of deposit of the stool in the presence of the inhibitor, whereas it is maintained in the bacterial colonies, whether the inhibitor is present or absent. The free enzymes in the stools are therefore clearly inhibited by the inhibitor, whereas the enzymes originating from the bacteria are not inhibited. These results demonstrate the aspecific enzymatic reactions due to the presence of "free enzymes" are greatly inhibited in the presence of the inhibitor O,O-di-(2-chloroethyl)-O-(3-chloro-4-methyl-coumarin-7-yl)phosphate, which limits the detection of false positives.

EXAMPLE 4

Inhibition of Free Esterases in a Sample, with O,O-diethyl p-nitrophenyl phosphate, O,O-dimethyl p-nitrophenyl phosphate and O,O-di(2-chloroethyl)-O-(3-chloro-4-methylcoumarin-7-yl)phosphate During the Identification of Yeast The aim of the experiments presented in this example is to demonstrate the free esterase-inhibiting effect of O,O-diethyl p-nitrophenyl phosphate, O,O-dimethyl p-nitrophenyl phosphate and O,O-di-(2-chloroethyl)-O-(3-chloro-4-methylcoumarin-7-yl)phosphate on stools contaminated with *Candida* yeast.

Preparation of the detection medium: A volume of 250 ml of detection medium is prepared from a powdered medium having the following composition:

| | |
|---|---|
| Peptones | 10 g/l |
| Glucose | 1 g/l |
| Tris | 0.16 g/l |
| Agar | 14 g/l |

Melting is carried out at 100° C., and the medium is autoclaved at 121° C. for 15 minutes. The additives are then added to the medium: Magenta C8 (500 mg/l; B-7102, BIOSYNTH, Staad, Switzerland); X-glucoside (75 mg/l; B-7250, BIOSYNTH, Staad, Switzerland); cefsulodine (10 mg/l; C 4786, Sigma, St Quentin Fallavier, France), and also the esterase inhibitor:

➢O,O-diethyl p-nitrophenyl phosphate: 5 mg/l
➢O,O-dimethyl p-nitrophenyl phosphate: 25 mg/l or
➢O,O-di-(2-chloroethyl)-O-(3-chloro-4-methylcoumarin-7-yl)phosphate: 75 mg/l The various selection media thus obtained are then poured into Petri dishes.

Seeding of yeast of the Candida genus: 10 μl of stools are deposited onto a Petri dish, and this stool suspension is mixed or not mixed with 10 μl of a suspension of *Candida* and isolated as 3 dials on a Petri dish. Various stools and various strains of *Candida* genus originating from the applicant's collection are used according to this protocol. The Petri dishes are incubated at 37° C. for 24 hours.

The appearance of a coloration at the point of deposit of the stool and in the *Candida* colonies is read according to a semi-quantitative scale:
0=absence of coloration
0.5=trace coloration
1=weak coloration
2=strong coloration.
The results are given in Table 4.

TABLE 4

Effects of the inhibitors O,O-diethyl p-nitrophenyl phosphate, O,O-dimethyl p-nitrophenyl phosphate, O,O-di-(2-chloroethyl)-O-(3-chloro-4-methylcoumarin-7-yl) phosphate on the activity of the free esters in a sample during the identification of *Candida* yeast

| Strain No. | Stool No. | No inhibitor Deposit | Colonies | O,O-Diethyl p-nitrophenyl phosphate: 5 mg/l Deposit | Colonies | O,O-Dimethyl p-nitrophenyl phosphate: 25 mg/l Deposit | Colonies | O,O-Di-(2-chloroethyl)-O-(3-chloro-4-methylcoumarin-7-yl) phosphate: 75 mg/l Deposit | Colonies |
|---|---|---|---|---|---|---|---|---|---|
| Absent | A | 2 | 0 | 0 | 0 | 0 | 0 | 0 | 0 |
|  | B | 1 | 0 | 0 | 0 | 0 | 0 | 0 | 0 |
| *Candida albicans* | A | 2 | 1 | 1 | 1 | 1 | 1 | 1 | 1 |
|  | B | 2 | 0.5 | 1 | 0.5 | 1 | 0.5 | 1 | 0.5 |
| *Candida dubliniensis* | A | 2 | 2 | 1 | 0.5 | 1 | 1 | 1 | 1 |
|  | B | 2 | 1 | 1 | 0.5 | 1 | 1 | 1 | 1 |
| *Candida krusei* | A | 2 | 1 | 1 | 0.5 | 1 | 0.5 | 1 | 0.5 |
|  | B | 2 | 1 | 1 | 0.5 | 1 | 0.5 | 1 | 0.5 |

As shown in Table 4, the coloration is decreased at the point of deposit of the stool in the presence of the various inhibitors, whereas it is maintained in the yeast colonies, whether the inhibitor is present or absent. The free enzymes in the stools are therefore clearly inhibited by the inhibitor, whereas the enzymes originating from the yeast are not inhibited.

These results demonstrate that the aspecific enzymatic reactions due to the presence of "free enzymes" are greatly inhibited in the presence of the inhibitors O,O-diethyl p-nitrophenyl phosphate, O,O-dimethyl p-nitrophenyl phosphate and O,O-di-(2-chloroethyl)-O-(3-chloro-4-methylcoumarin-7-yl)phosphate, which limits the detection of false positives.

EXAMPLE 6

Inhibition of Free α-glucosidase in a Sample, with Castanospermine, during the Identification of Bacteria The aim of the experiments presented in this example is to demonstrate the inhibitory effect of castanospermine on the free α-glucosidase in a sample (stools) contaminated with *Staphylococcus aureus* strains.

Preparation of the detection medium: 250 ml of the medium of Example 1, in which the O,O-diethyl p-nitrophenyl phosphate is replaced with various concentrations of castanospermine: 0, 1, 2, 4 and 8 g/l, are prepared according to the method of Example 1.

The various detection media thus obtained are poured into Petri dishes.

Seeding of *Staphylococcus aureus* strains: The Petri dishes are inoculated, incubated and read as in Example 1.

The results obtained are given in Table 6.

TABLE 6

Effects of castanospermine on the activity of the free α-glucosidase enzymes in a sample during the identification of *Staphylococcus aureus* strains

| Strain No. | Stool No. | [Castanospermine] in g/l | | | | | | | | | |
|---|---|---|---|---|---|---|---|---|---|---|---|
|  |  | 0 | | 1 | | 2 | | 4 | | 8 | |
|  |  | Deposit | Colonies | Deposit | Colonies | Deposit | Colonies | Deposit | Colonies | Deposit | Colonies |
| Absence | A | 2 | 0 | 1 | 0 | 1 | 0 | 0.5 | 0 | 0 | 0 |
|  | B | 1 | 0 | 0.5 | 0 | 0.5 | 0 | 0 | 0 | 0 | 0 |
| *Staphylococcus aureus* No. 1 | A | 2 | 2 | 2 | 2 | 1 | 2 | 1 | 2 | 1 | 1 |

TABLE 6-continued

Effects of castanospermine on the activity of the free α-glucosidase enzymes in a sample during the identification of *Staphylococcus aureus* strains

| | | [Castanospermine] in g/l | | | | | | | | |
|---|---|---|---|---|---|---|---|---|---|---|
| | Stool | 0 | | 1 | | 2 | | 4 | | 8 |
| Strain No. | No. | Deposit | Colonies | Deposit | Colonies | Deposit | Colonies | Deposit | Colonies | Deposit | Colonies |
| *Staphylococcus aureus* n° 2 | B | 2 | 2 | 2 | 2 | 1 | 2 | 0.5 | 2 | 0 | 1 |

As shown in Table 6, the coloration is decreased at the point of deposit of the stool in the presence of castanospermine, whereas it is maintained in the bacterial colonies, whether the inhibitor is present or absent. The free enzymes in the stools are therefore clearly inhibited by the inhibitor, whereas the enzymes originating from the bacteria are not inhibited.

These results demonstrate that the aspecific enzymatic reactions due to the presence of "free enzymes" are greatly inhibited in the presence of the castanospermine inhibitor, which limits the detection of false positives.

It should be noted that a variant to Examples 1 to 6 consists in adding the inhibitor to the sample medium instead of adding it directly to the culture medium.

EXAMPLE 7

Method for Identifying Inhibitors of at Least a Second Enzyme According to the Invention This method consists in carrying out the experiment of Examples 1 or 2, replacing:
i) the culture media described (including the enzymatic substrates) with that which is suitable for the microorganisms sought;
ii) the stools with the sample in which said microorganisms are sought and which produces a parasitic reaction with one or more of the enzymatic substrates included in the medium;
iii) the inhibitor O,O-diethyl p-nitrophenyl phosphate, O,O-dimethyl p-nitrophenyl phosphate, O,O-di-(2-chloroethyl)-O-(3-chloro-4-methyl-coumarin-7-yl)phosphate or castanospermine, with a potential inhibitor to be tested at various concentrations.

The invention claimed is:

1. Medium for detecting and/or identifying a bacterium present in a sample, comprising:
   a culture medium,
   at least one substrate that can be hydrolysed to a labelled product by an esterase not free in the sample, and specific for said bacterium, wherein said bacterium is of a genus selected from the group consisting of *Salmonella* and *Staphylococcus*, and
   at least one inhibitor of at least a second enzyme, different from the first enzyme or identical to it, but free in said sample and not originating from said bacterium,
   wherein the inhibitor is a compound of formula (I)

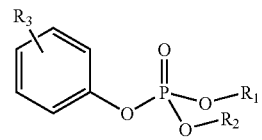

in which $R_1$ is a hydrogen atom, or an alkyl, aryl or halogen group,
$R_2$ is a hydrogen atom, or an alkyl, aryl or halogen group,
$R_3$ is nothing, or an alkyl, aryl or $NO_2$ group.

2. Detection and/or identification medium according to claim 1, wherein said bacterium belongs to the *Salmonella* genus.

3. Detection and/or identification medium according to claim 1, wherein the inhibitor is O,O-diethyl p-nitrophenyl phosphate and/or O,O-dimethyl p-nitrophenyl phosphate and/or O,O-di-(2-chloroethyl)-O-(3-chloro-4-methylcoumarin-7-yl) phosphate and/or at least one derivative of these molecules.

4. Detection and/or identification medium according to claim 3, wherein the concentration of O,O-diethyl p-nitrophenyl phosphate or its derivative in the detection medium is between 0.1 and 15 mg/l.

5. Detection and/or identification medium according to claim 3, wherein the concentration of O,O-dimethyl p-nitrophenyl phosphate or its derivative in the detection medium is between 0.1 and 100 mg/l.

6. Detection and/or identification medium according to claim 3, wherein the concentration of O,O-di-(2-chloroethyl)-O-(3-chloro-4-methylcoumarin-7-yl) phosphate or its derivative in the detection medium is between 1 and 1000 mg/l.

7. Medium for detecting and/or identifying a bacterium present in a sample, comprising:
   a culture medium,
   at least one substrate that can be hydrolysed to a labelled product by an osidase not free in the sample, and specific for said bacterium, wherein said bacterium is of a genus selected from the group consisting of *Salmonella* and *Staphylococcus*, and
   at least one inhibitor of at least a second enzyme, different from the first enzyme or identical to it, but free in said sample and not originating from said bacterium, wherein the inhibitor is a compound of formula (II):

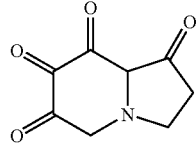

or a derivative of this compound.

8. Detection and/or identification medium according to claim 7, wherein the concentration of compound of formula (II) or its derivative in the detection medium is between 1 and 10 g/l.

9. Detection and/or identification medium according to claim 1, wherein said substrate is a chromogenic substrate.

10. Method for detecting and/or identifying a bacterium, comprising:
seeding the a bacterium to be identified onto a detection medium, according to claim 1,
incubating the detection medium seeded with the bacterium to be identified, and
determining the presence of said bacterium by detecting the substrate(s) hydrolysed to a labelled product.

11. Detection and/or identification medium according to claim 1, wherein said second enzyme is an esterase.

12. Detection and/or identification medium according to claim 7, wherein said second enzyme is an osidase.

13. Detection and/or identification medium according to claim 1, wherein said bacterium belongs to the *Staphylococcus* genus.

14. Detection and/or identification medium according to claim 7, wherein said bacterium belongs to the *Salmonella* genus.

15. Detection and/or identification medium according to claim 7, wherein said bacterium belongs to the *Staphylococcus* genus.

* * * * *